(12) United States Patent
Bernhard et al.

(10) Patent No.: US 11,733,165 B2
(45) Date of Patent: Aug. 22, 2023

(54) OPTICAL SENSOR, METHOD AND USE OF THE SENSOR

(71) Applicant: Endress+Hauser Conducta GmbH+Co. KG, Gerlingen (DE)

(72) Inventors: Ralf Bernhard, Stuttgart (DE); Manfred Jagiella, Notzingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 99 days.

(21) Appl. No.: 17/388,138

(22) Filed: Jul. 29, 2021

(65) Prior Publication Data

US 2022/0042909 A1 Feb. 10, 2022

(30) Foreign Application Priority Data

Aug. 4, 2020 (DE) ..................... 10 2020 120 591.0

(51) Int. Cl.
*G01N 21/64* (2006.01)
*G01N 33/18* (2006.01)

(52) U.S. Cl.
CPC ....... *G01N 21/645* (2013.01); *G01N 33/1833* (2013.01); *G01N 2201/062* (2013.01)

(58) Field of Classification Search
CPC ............. G01N 21/645; G01N 33/1833; G01N 2201/062
See application file for complete search history.

(56) References Cited

U.S. PATENT DOCUMENTS

| | | |
|---|---|---|
| 6,013,228 A | 1/2000 | Achter et al. |
| 2004/0106211 A1 | 6/2004 | Kauer et al. |
| 2005/0122225 A1 | 6/2005 | Kram et al. |
| 2005/0236481 A1* | 10/2005 | Gascoyne ............ G11B 19/122 235/468 |
| 2019/0017872 A1 | 1/2019 | Brunson et al. |
| 2019/0186995 A1 | 6/2019 | Brunson et al. |

FOREIGN PATENT DOCUMENTS

JP 2002168789 A * 6/2002 ............. G01N 21/64

OTHER PUBLICATIONS

Benito et al, "Multi-Analysis Laser Spectrofluorometry System for Oils", Apr. 2, 2015 (Year: 2015).*

* cited by examiner

*Primary Examiner* — David P Porta
*Assistant Examiner* — Fani Polyzos Boosalis
(74) *Attorney, Agent, or Firm* — Christopher R. Powers; Endress+Hauser (USA) Holding, Inc.

(57) ABSTRACT

An optical sensor for determining the concentration of polycyclic aromatic hydrocarbons in a medium incudes a light source configured to emit transmitted light having a wavelength of less than 300 nm into the medium; a detector for receiving received light, wherein the detector is configured at least for receiving received light having a wavelength of 300 nm to 400 nm, wherein the transmitted light is converted into received light by means of fluorescence in the medium as a function of the concentration of polycyclic aromatic hydrocarbons, wherein a detector signal is generated from the received light; and a data processing unit configured to determine the concentration of polycyclic aromatic hydrocarbons using the detector signal, wherein the data processing unit controls the light source such that the light source emits modulated transmitted light according to a duty cycle. Methods of using the optical sensor are further disclosed.

17 Claims, 3 Drawing Sheets

OPTICAL SENSOR, METHOD AND USE OF THE SENSOR

CROSS-REFERENCE TO RELATED APPLICATION

The present application is related to and claims the priority benefit of German Patent Application No. 10 2020 120 591.0, filed on Aug. 4, 2020, the entire contents of which are incorporated herein by reference.

TECHNICAL FIELD

The present disclosure relates to an optical sensor for determining the concentration of polycyclic aromatic hydrocarbons in a medium.

BACKGROUND

In conventional fluorescence measurement, the medium is generally irradiated with a shortwave excitation light (transmitted light) and the longer-wave fluorescent light (received light) that is generated by the medium and that is generated as a function of the concentration of the species to be measured is detected. Such a fluorescence sensor comprises a light source and a detector. The light source transmits transmitted light; the detector receives received light. Since the fluorescent light is emitted in all spatial directions, the light paths of the transmitted and received light can in principle be at any angle to one another.

Excitation light of as high an intensity as possible and therefore a correspondingly strong light source are needed to measure small substance concentrations. The ideal excitation wavelength is a function of the substance that is to be measured. Gas discharge lamps are usually used. However, these are relatively large, require a relatively complicated electrical control, and above all require a lot of energy.

SUMMARY

The present disclosure is based on the object of proposing a compact, low-energy and, at the same time, long-lasting optical fluorescence sensor.

The object is achieved by an optical sensor for determining the concentration of polycyclic aromatic hydrocarbons in a medium, comprising a light source, wherein the light source comprises a light-emitting diode (an LED), wherein the LED emits transmitted light having a wavelength of less than 300 nm, for example, 255 nm and/or 270 nm, into the medium; a detector for receiving received light, wherein the detector is designed at least for receiving received light having a wavelength of, for example, 300 nm to 400 nm, wherein the transmitted light is converted into received light by means of fluorescence in the medium as a function of the concentration of polycyclic aromatic hydrocarbons, wherein a detector signal can be generated from the received light; and a data processing unit, which determines the concentration of polycyclic aromatic hydrocarbons by means of the detector signal, wherein the data processing unit controls the light source in such a way that it emits modulated transmitted light, wherein the data processing unit controls the light source with a duty cycle.

One embodiment provides that the data processing unit changes the duty cycle as a function of the concentration, the change, and/or the rate of change of the concentration.

One embodiment provides that the data processing unit controls the light source in such a way that it transmits a pulse-frequency-modulated burst signal having the duty cycle as transmitted light.

One embodiment provides that the data processing unit controls the light source in such a way that it transmits a pulse-width-modulated burst signal having the duty cycle as transmitted light.

One embodiment provides that the sensor comprises a temperature sensor which measures the temperature of the light source, wherein the data processing unit changes the duty cycle of the transmitted light as a function of the temperature.

One embodiment provides that the sensor comprises a monitor diode, wherein the monitor diode monitors the transmission power of the light source, wherein the data processing unit changes the duty cycle of the transmitted light as a function of the transmission power.

One embodiment provides that the sensor comprises an operating time counter, for example, as part of the data processing unit, wherein the data processing unit changes the duty cycle of the transmitted light as a function of the operating time.

The object is furthermore achieved by a method for determining the concentration of polycyclic aromatic hydrocarbons in a medium, comprising the steps of: emitting modulated transmitted light having a duty cycle with a light source designed as an LED into the medium, wherein the transmitted light has a wavelength of less than 300 nm, for example, 255 nm and/or 270 nm; converting transmitted light into received light by means of fluorescence in the medium as a function of the concentration of polycyclic aromatic hydrocarbons; and generating a detector signal from the received light and determining the concentration of the polycyclic aromatic hydrocarbons.

One embodiment provides the step of: changing the duty cycle of the light source as a function of the concentration of the polycyclic aromatic hydrocarbons, their change, their rate of change, the temperature of the light source, the operating time of the light source, and/or the transmission power of the light source.

The object is furthermore achieved by using the sensor as described above to determine the oil-in-water content.

The object is furthermore achieved by using the sensor as described above for scrubbing the flue gas.

Flue gas scrubbing is the cleaning of exhaust gases, for example, in ships. Ships expel smoke and soot since they often use heavy oil as fuel, which is dirty, harmful to the environment, and also toxic in some instances. The exhaust gases are passed through a water cascade for "scrubbing." For the most part, the exhaust gases include various polycyclic aromatic hydrocarbons (PAHs for short). The PAHs are washed out during flue gas scrubbing. They form during incomplete combustion. The irrigation is carried out by seawater, which ultimately flows back into the sea. By using the sensor in flue gas scrubbing, the PAH content can be ascertained and it can thus be ensured that only water which conforms to legal requirements flows back into the sea. The measurement can be carried out by means of fluorescence.

Polycyclic aromatic hydrocarbons form a substance group of organic compounds consisting of at least two bonded aromatic ring systems, which always lie in one plane. The simplest PAH is naphthalene, in which two benzene rings are fused via a common bond, also referred to as condensed ring systems. Fluorene is also a PAH since both rings are rigidly connected to one another by the additional methylene unit. These annular hydrocarbons may additionally carry substituents (often methyl groups). In an extended designation, PAHs include derivatives having heteroatoms (primarily oxygen and nitrogen) in the form of aldehyde, keto, carboxy, and nitro groups but also heteroaromatics. PAH are predominantly neutral, non-polar solids. Many exhibit fluorescence. PAHs are only very slightly soluble in water; as the number of condensed rings increases, volatility and solubility decrease (in organic solvents as well). Additional PAHs are, for example, anthracene, benzopyrene, acenaphthylene, acenaphthene, phenanthrene, fluoranthene, pyrene, benzanthracene, coronene, ovalene, tetracene, pentacene, or chrysene. PAHs are natural components of coal and petroleum. Traces of PAH can be found in gasoline and diesel fuel or fuel oil. PAHs are also found in tobacco smoke and smoked, grilled, and roasted meat. PAHs can also accumulate in house dust on high-traffic roads.

BRIEF DESCRIPTION OF THE DRAWINGS

What was described above is explained in more detail based on the following figures.

In the figures, the same features are identified by the same reference signs.

DETAILED DESCRIPTION

Figure 1:
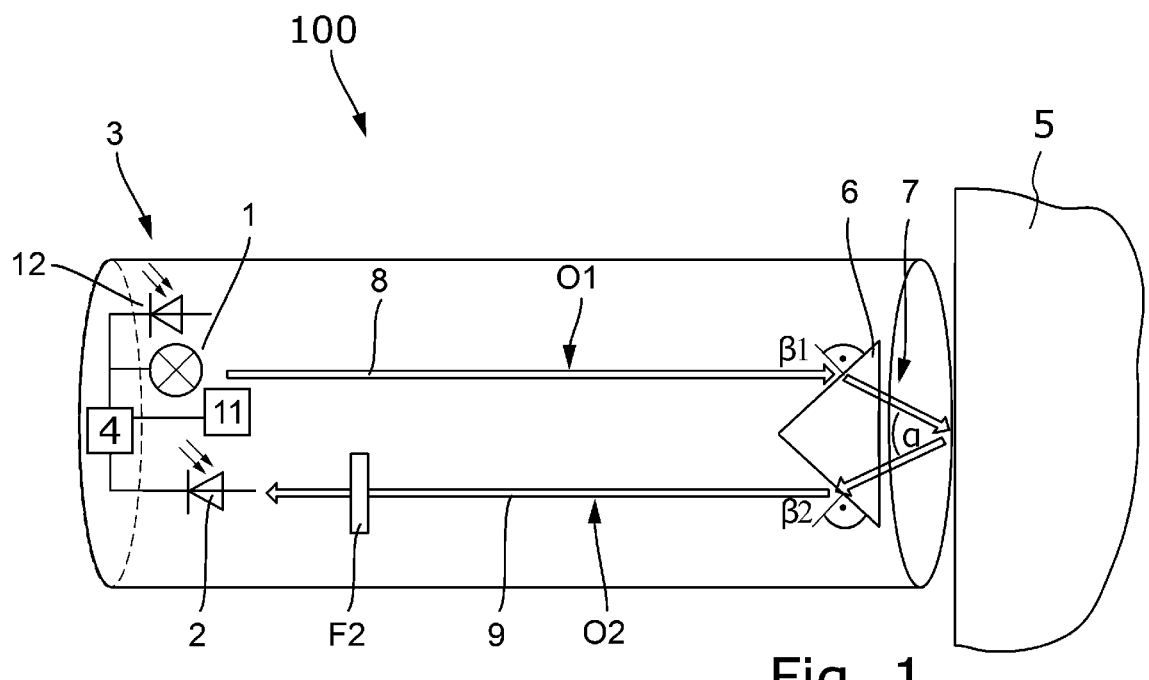
FIG. 1 shows a sensor of the present disclosure in a symbolic cross-section.
Figure 3:
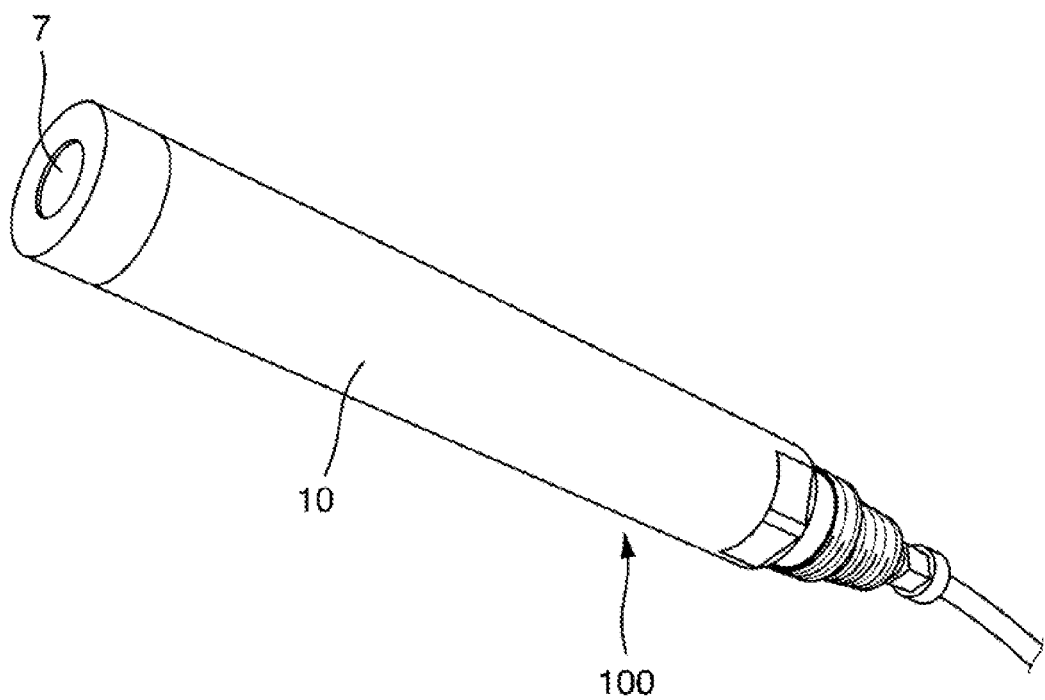
FIG. 3 shows an embodiment of a sensor of the present disclosure.

The entirety of a sensor assembly of the present disclosure is denoted by reference sign 100, includes a sensor 3, and is shown schematically in FIG. 1. FIG. 3 shows the sensor 100 in a housing 10 with the optical window 7.

In principle, the sensor 3 is suitable for determining the oil-in-water content of a medium 5 or for determining the PAH content in the flue gas scrubbing, for example, on ships.

A light source 1 transmits transmitted light 8 toward the medium 5. The light source 1 may be an LED which emits light having a wavelength of 250-260 nm, for example, 255 nm.

In one embodiment, the sensor 3 comprises a second light source (e.g., a second LED) which emits transmitted light having a wavelength of 270 nm.

Figure 4:
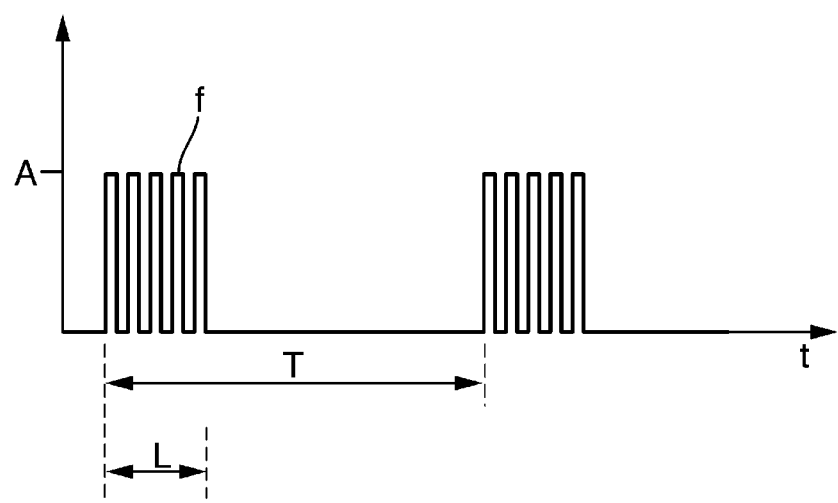
FIG. 4 shows a modulation and a duty cycle.

The sensor 3 comprises a data processing unit 4, for example a microcontroller. The data processing unit 4 controls the light source 1 in such a way that it emits modulated transmitted light 8 and that the light source 1 emits transmitted light 8 with a duty cycle T. A pulse-frequency-modulated burst signal with the duty cycle T is shown in FIG. 4. The light source 1 is operated with an adjustable current source. The amplitude A is approximately proportional to the operating current of the light source 1. The modulation frequency f and burst length L are not generally changed. For example, the modulation frequency is f=3 kHz. Duty cycle is, for example, 10% at a burst length of 100 ms. A pulse-frequency-modulated burst signal may also be used.

The duty cycle is changed as a function of the concentration of the polycyclic aromatic hydrocarbons, their change, their rate of change, the temperature of the light source 1, the operating time of the light source 1, and/or the transmission power of the light source 1 (see below).

The transmitted light 8 strikes a prism 6 at an angle β1. The prism 6 is a right-angled prism, for example. The base points toward the medium to be measured. A first optical path O1 from the light source 1 to the prism 6 is defined. The optical path O1 may also contain one or more lenses L1 or filters F1 (see below).

The transmitted light 8 is partially converted into received light 9 in the medium 5 by fluorescence as a function of the concentration of polycyclic aromatic hydrocarbons in the medium 5. The received light 9 takes the path toward the detector 2 via the prism 6. The received light 9 exits the prism at an angle β2. The detector 2 may be a photodiode which receives the received light 9 at a wavelength of 300-400 nm. A second optical path O2 is defined from the prism 6 to the detector 2. The optical path O2 may also contain one or more lenses L2 or filters F2 (see below). The first and second optical paths O1, O2 are substantially parallel to each other on the side of the prism facing away from the medium.

The sensor 3 comprises a monitor diode 12, which monitors the transmission power of the light source 1.

The sensor 3 comprises a temperature sensor 11 which measures the temperature of the light source 1.

The sensor 3 comprises an operating time counter as part of the data processing unit 4, which counts the operating time of the light source 1.

The light source 1, prism 6, and detector 2 are arranged in a housing 10. The housing may be tube-shaped, having a diameter of 35-75 mm. The housing 10 comprises the optical window 7, which is transmissive at least to transmitted light 8 and received light 9, wherein the prism 6 and the window 7 are either cemented, glued, joined together (e.g., fused), or manufactured from one piece. In one embodiment, the individual components are separate. The distance from the light source 1 or the detector 2 to the window 7 is about 2-6 cm.

The filter or filters F1, F2 are designed as wavelength filters, for example, as interference filters.

Figure 2:
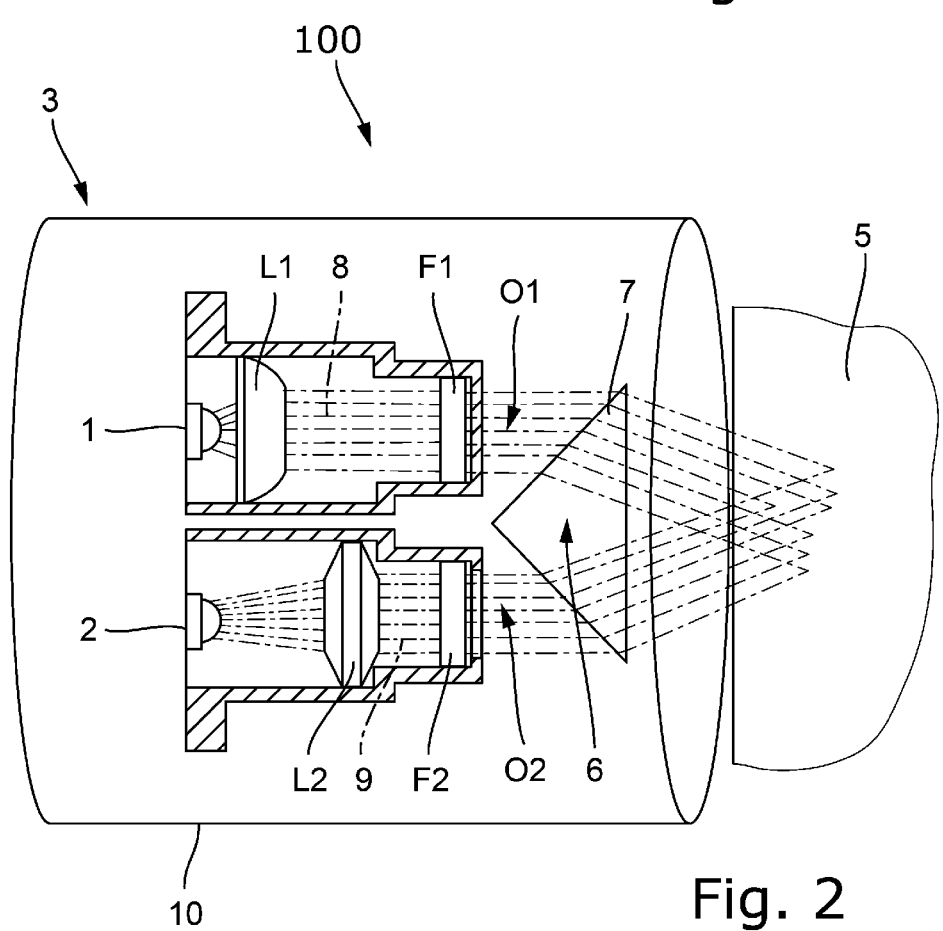
FIG. 2 shows an optical simulation of the beam path.

FIG. 2 shows an optical simulation of the sensor 3. Transmitted light 8 from the light source 1 is first transmitted through a lens L1, then through a filter F1. After fluorescence at the medium 5, received light 9 first passes through the filter F2, then the lens L2. Lenses L1, L2 ensure that only substantially parallel light strikes the filters F1 and F2.

The lenses L1, L2 have focal lengths between 2-20 mm. Since the optical paths O1 and O2 run in parallel, the lenses L1 and L2 have a diameter of at most half the diameter of the housing 10, for example, 15-40 mm.

In addition, the light source 1 is preferably approximately at the focal point of the lens L1 and the detector 2 is preferably approximately at the focal point of the lens L2.

In one exemplary embodiment, the diameter of the housing 10 is smaller than that described above, for instance, from the range 8-15 mm, for example, 12 mm. The principle described above with the first and second optical paths O1 and O2 running in parallel and also with the prism 6 can also be used in such an embodiment. In one embodiment, the light source 1 and the detector 2 as well as the lenses L1, L2 and the filters F1, F2 are arranged outside the housing 10 due to the smaller diameter. In one embodiment, the lenses L1, L2 and the filters F1, F2 can be dispensed with. In this case, one or both optical paths O1 and/or O2 can be designed by means of optical waveguides or as free beams. The transmitted light 8 is converted into received light 9 in the medium 5. In the medium 5, a portion of the transmitted light 8 is absorbed and a portion is scattered. The portion scattered at an angle α is the received light 9, which is received by the detector 2 after passing through the prism 6.

We claim:

1. An optical sensor for determining a concentration of polycyclic aromatic hydrocarbons in a medium, the sensor comprising:
- a light source adapted to emit transmitted light having a wavelength of less than 300 nm into the medium;
- a detector configured to receive and detect at least received light from the medium, the received light having a wavelength of 300 nm to 400 nm, wherein the transmitted light is converted into the received light via fluorescence in the medium as a function of the concentration of polycyclic aromatic hydrocarbons, and wherein the detector is configured to generate a detector signal in response to the received light; and
- a data processing unit configured to determine the concentration of polycyclic aromatic hydrocarbons using the detector signal, wherein the data processing unit is further configured to control the light source as to modulate the emitted transmitted light, and wherein the data processing unit controls the light source according to a duty cycle.

2. The sensor of claim 1, wherein the data processing unit is configured to change the duty cycle as a function of the concentration, a change in the concentration, and/or a rate of change of the concentration.

3. The sensor of claim 1, wherein the data processing unit is configured to control the light source such that the light source emits a pulse-frequency-modulated burst signal having the duty cycle as the transmitted light.

4. The sensor of claim 1, further comprising a temperature sensor adapted to measure a temperature of the light source, wherein the data processing unit is further configured to change the duty cycle as a function of the temperature.

5. The sensor of claim 1, further comprising a monitor diode configured to monitor a transmission power of the light source, wherein the data processing unit is further configured to the duty cycle as a function of the transmission power.

6. The sensor of claim 1, further comprising an operating time counter configured to count a cumulative operating time of the light source, wherein the data processing unit is further configured to change the duty cycle as a function of the cumulative operating time.

7. The sensor of claim 6, wherein the operating time counter is part of the data processing unit.

8. The sensor of claim 1, wherein the light source comprises a light-emitting diode.

9. The sensor of claim 1, wherein the transmitted light has a wavelength of 255 nm and/or 270 nm.

10. A method, comprising determining an oil-in-water content of a medium using the sensor of claim 1.

11. The method of claim 10, wherein the data processing unit is configured to change the duty cycle as a function of the oil-in-water content, a change in the oil-in-water content, and/or a rate of change of the oil-in-water content.

12. The method of claim 10, wherein the data processing unit is configured to control the light source such that the light source emits a pulse-frequency-modulated burst signal having the duty cycle as the transmitted light.

13. A method for determining a concentration of polycyclic aromatic hydrocarbons in a medium, the method comprising:
- emitting modulated transmitted light from a light source having a duty cycle, wherein the transmitted light has a wavelength of less than 300 nm;
- converting transmitted light into received light via fluorescence in the medium as a function of the concentration of polycyclic aromatic hydrocarbons; and
- generating a detector signal from the received light and determining the concentration of the polycyclic aromatic hydrocarbons using the detector signal.

14. The method of claim 13, wherein the light source comprises a light-emitting diode.

15. The method of claim 13, wherein the transmitted light has a wavelength of 255 nm and/or 270 nm.

16. The method of claim 13, further comprising changing the duty cycle of the light source as a function of the concentration of the polycyclic aromatic hydrocarbons, a change in the concentration, a rate of change of the concentration, a temperature of the light source, an operating time of the light source, and/or a transmission power of the light source.

17. The method of claim 13, further comprising determining the concentration of the polycyclic aromatic hydrocarbons using the detector signal in a flue gas scrubbing process.

* * * * *